US00PP23614P2

(12) United States Plant Patent
Bruinen

(10) Patent No.: US PP23,614 P2
(45) Date of Patent: May 21, 2013

(54) ***ZAMIOCULCAS ZAMIIFOLIA* PLANT NAMED 'LUCKYWHIT'**

(50) Latin Name: *Zamioculcas zamiifolia*
Varietal Denomination: LUCKYWHIT

(75) Inventor: Edward Bruinen, Maasdijk (NL)

(73) Assignee: Edplant B.V., Maasdijk (NL)

( * ) Notice: Subject to any disclaimer, the term of this patent is extended or adjusted under 35 U.S.C. 154(b) by 0 days.

(21) Appl. No.: 13/374,455

(22) Filed: Dec. 28, 2011

(51) Int. Cl.
*A01H 5/00* (2006.01)

(52) U.S. Cl.
USPC ..... Plt./263.1

(58) Field of Classification Search ..... Plt./263.1
See application file for complete search history.

*Primary Examiner* — Annette Para
(74) *Attorney, Agent, or Firm* — Cassandra Bright

(57) ABSTRACT

A new and distinct *Zamioculcas zamiifolia* cultivar named 'LUCKYWHIT' is disclosed, characterized by variegated leaves and a curled leaf margin. The new variety is a *Zamioculcas zamiifolia*, normally produced as an ornamental plant.

1 Drawing Sheet

Latin name of the genus and species: *Zamioculcas zamiifolia.*

Variety denomination: 'LUCKYWHIT'.

BACKGROUND OF THE INVENTION

The new *Zamioculcas zamiifolia* cultivar is a product of a chance discovery by the inventor, Edward Bruinen, in Maasdijk, The Netherlands. The inventor identified and selected the interesting mutation of *Zamioculcas zamiifolia* and proceeded to test its suitability for ornamental commercial applications.

The parent is an unpatented, unnamed variety of *Zamioculcas zamiifolia*. The new variety was discovered in August 2007 by the inventor as a naturally occurring whole plant mutation, in a commercial greenhouse in Maasdijk, The Netherlands.

Asexual reproduction of the new cultivar 'LUCKYWHIT' by vegetative cuttings was first performed at a commercial greenhouse in Maasdijk, The Netherlands in September 2007 and has shown that the unique features of this cultivar are stable and reproduced true to type in successive generations.

SUMMARY OF THE INVENTION

The cultivar 'LUCKYWHIT' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LUCKYWHIT' These characteristics in combination distinguish 'LUCKYWHIT' as a new and distinct *Zamioculcas zamiifolia* cultivar:

1. Variegated leaves
2. Curled leaf margin

Plants of the new cultivar 'LUCKYWHIT' are similar to plants of the parent, *Zamioculcas zamiifolia*. in most horticultural characteristics, however, plants of the new cultivar 'LUCKYWHIT' produce variegated leaves compared to green leaves. Also the leaf margin of 'LUCKYWHIT' is curled whereas the parent is not.

COMMERCIAL COMPARISON

Plants of 'LUCKYWHIT' are best compared to the parent variety.

BRIEF DESCRIPTION OF THE PHOTOGRAPHS

The accompanying photograph in FIG. 1 illustrates in full color a typical plant of 'LUCKYWHIT' grown in a greenhouse, in a 17 cm pot. Age of the plant photographed is approximately 18 months from a rooted cutting.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'LUCKYWHIT' plants grown in a greenhouse, in Maasdijk, The Netherlands. The growing temperature ranged from 20° C. during the day to 18° C. during the night. General light conditions are normal sunlight. Measurements and numerical values represent averages of typical plant types. Plants are approximately 18 months old from a rooted cutting.

Botanical classification: *Zamioculcas zamiifolia* 'LUCKYWHIT'.

PROPAGATION

Time to initiate roots: About 14-21 days at approximately 22° C.

Root description: Moderately free branched, thick, non-fibrous, non-fleshy, coloured grey-brown; 199B.

Time to produce rooted plantlet: Approximately 4-5 weeks at approximately 22 ° C.

PLANT

Growth habit: Upright, narrow inverted triangular.
Plant shape: Narrow inverted triangular.
Height: Approximately 58.1 cm to top of highest leaf.
Plant spread: Approximately 28.9 cm in a 17 cm pot.
Growth rate: Moderate.
Branching characteristics: Not branching, leaves grow directly from a basal clump.
Number of clumps: Average: 1.
Number of leaves per clump: Average 5.
Age of plant described: Approximately 18 months.

FOLIAGE

Leaf:
*Arrangement*.—Leaves alternately paripinnate.
*Average length(excluding petiole)*.—Approximately 33.7 cm (measured from lowest leaflet to top).
*Average width*.—Approximately 14.3 cm.
Leaflets:
*Shape of blade*.—Leaflets ovate to elliptic.
*Average length*.—Approximately 7.4 cm.
*Average width*.—Approximately 4.6 cm.
*Aspect*.—Flat to somewhat undulating along margin.
*Apex*.—Abruptly acute.
*Base*.—Rounded.
*Margin*.—Entire.
*Texture of top surface*.—Smooth, very glossy.
*Texture of bottom surface*.—Smooth, very glossy (but slightly less than upper side).
*Color*.—Young foliage upper side: Near RHS Green N137C, upper ⅔ of leaf blade heavily blotched and marbled with RHS Yellow-Green 144B and 144C. Young foliage under side: Near RHS Green 141A, upper ⅓ of leaf blade heavily blotched and marbled RHS 143B. Mature foliage upper side: Near RHS Green 143A, outer (marginal) ⅔ of leaf blade heavily blotched and marbled RHS Yellow-Green 151C and 151D. Mature foliage under side: Near RHS Green 143A, upper ⅓ of leaf blade heavily blotched and marbled 144C.
Venation:
*Type*.—Pinnate.
*Venation coloration upper side*.—Near RHS Green 143B.
*Venation coloration under side*.—Near RHS Yellow-Green 144B.
Rachis:
*Length*.—Approximately 40.0 cm.
*Width*.—At narrowest point: Approximately 0.4 cm. Above clump: Approximately 2.4 cm.
*Color*.—Near RHS Yellow-Green 148B.
*Strength*.—Very strong.
*Texture*.—Smooth, dull, glabrous.
Other structures: None present.

FLOWER

Typically non flowering. No flowers, no reproductive organs observed.

OTHER CHARACTERISTICS

Seed production: Not observed to date.
Disease resistance: Neither resistance nor susceptibility to diseases or pests has been observed in this variety.
Temperature tolerance: Low temperature tolerance to at least 5° C., high temperatures to at least 40° C.
Drought tolerance: Moderate tolerance for drought.

What is claimed is:

1. A new and distinct cultivar of *Zamioculcas zamiifolia* plant named 'LUCKYWHIT' as herein illustrated and described.

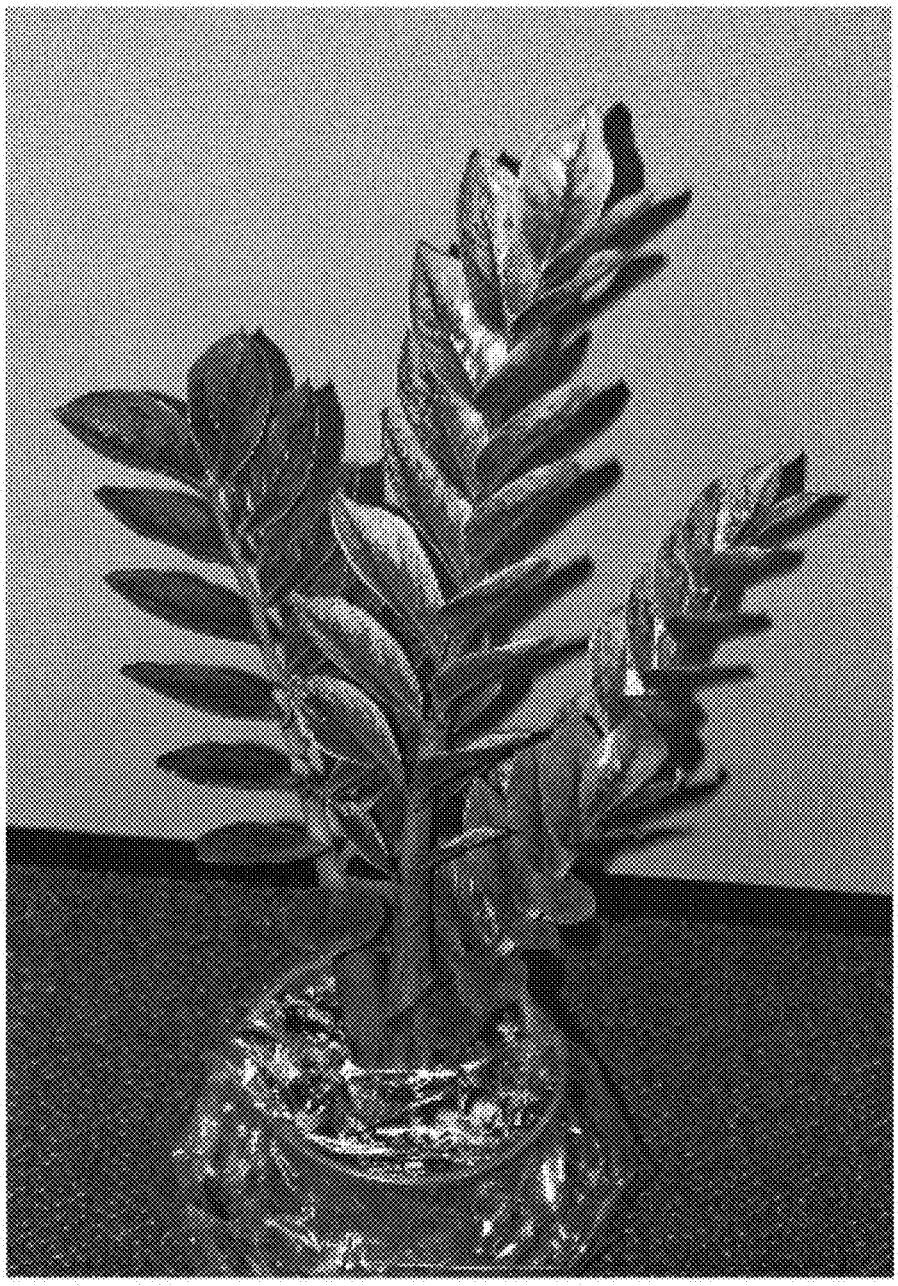

* * * * *